(12) United States Patent
Doi et al.

(10) Patent No.: US 8,979,042 B2
(45) Date of Patent: Mar. 17, 2015

(54) AUTOMATIC BALANCING STRUCTURE OF MEDICAL BALANCING STAND

(71) Applicant: Mitaka Kohki Co., Ltd., Tokyo (JP)

(72) Inventors: Masao Doi, Tokyo (JP); Yusuke Nakata, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 0 days.

(21) Appl. No.: 14/095,467

(22) Filed: Dec. 3, 2013

(65) Prior Publication Data

US 2014/0157937 A1 Jun. 12, 2014

(30) Foreign Application Priority Data

Dec. 7, 2012 (JP) ................................. 2012-268091

(51) Int. Cl.
*F16M 11/00* (2006.01)
*B25J 19/00* (2006.01)

(52) U.S. Cl.
CPC ............ *B25J 19/0008* (2013.01); *Y10S 901/27* (2013.01); *Y10T 74/20305* (2013.01)
USPC ................... 248/162.1; 248/123.11; 248/404; 901/27

(58) Field of Classification Search
USPC .............. 248/162.1, 123.11, 404, 406.2, 410, 248/417
See application file for complete search history.

(56) References Cited

U.S. PATENT DOCUMENTS 5,613,419 A * 3/1997 Pierson et al. .................. 91/361
7,554,321 B2 * 6/2009 Holt et al. ................. 324/759.03

FOREIGN PATENT DOCUMENTS

JP 2005-052679 3/2005

OTHER PUBLICATIONS

U.S. Appl. No. 14/093,156 to Masao Doi et al., filed Nov. 29, 2013.

* cited by examiner

*Primary Examiner* — Amy J. Sterling
(74) *Attorney, Agent, or Firm* — Greenblum & Bernstein, P.L.C.

(57) ABSTRACT

An automatic balancing structure of a medical balancing stand has stoppers arranged on a turn plate. In a normal state, the stoppers are in contact with and hold a contact part of a lever so that the lever and turn plate follow a rotative motion of a lateral arm. If the lateral arm causes an imbalance, a strain occurs on the lever to which a strain sensor is attached. The strain sensor detects the strain and outputs a signal to an adjustment unit so as to cancel the imbalance of the lateral arm. The strain sensor helps downsizing the automatic balancing structure and making the balance adjustment easier.

2 Claims, 6 Drawing Sheets

AUTOMATIC BALANCING STRUCTURE OF MEDICAL BALANCING STAND

BACKGROUND OF THE INVENTION

1. Field of the Invention

The present invention relates to an automatic balancing structure of a medical balancing stand.

2. Description of Related Art

The medical balancing stand is used to support and suspend a medical device such as a surgical microscope at an optional position in midair. The medical balancing stand includes a vertical arm and a lateral arm. A first end of the lateral arm supports a relatively heavy load such as a surgical microscope and a second end of the lateral arm supports a counterweight to balance the load. An intermediate part of the lateral arm is provided with a turn shaft that is horizontally supported with the vertical arm so that the lateral arm is able to turn relative to the vertical arm.

The turn shaft has a clutch unit that is locked in a normal state to prevent the lateral arm from turning relative to the vertical arm. When moving the load (for example, a surgical microscope) supported at the first end of the lateral arm to an optional height position, an operator who may be a doctor releases the clutch unit and turns the surgical microscope together with the lateral arm. The lateral arm having the surgical microscope is balanced on the turn shaft due to the counterweight, and therefore, stops at an optional turned position in midair as if in a gravity-free state even if the operator removes his or her hands from the surgical microscope. Accordingly, the operator is able to freely change the position of the surgical microscope in midair. Once the position and orientation of the surgical microscope are optimized as required, the operator locks the clutch unit to fix the lateral arm at the position.

Balance of the lateral arm on the turn shaft is detected and adjusted with the use of an encoder that detects a turn angle of the turn shaft and a computer that adjusts the counterweight according to a signal from the encoder. In connection with this, a related art is disclosed in, for example, Japanese Unexamined Patent Application Publication No. 2005-52679.

SUMMARY OF THE INVENTION

The related art that employs the encoder and computer to balance the lateral arm is large and needs a complicated adjusting operation. If the lateral arm is a multi-joint arm having a plurality of horizontal turn shafts, the related art must conduct further complicated operations because it must detect a turn angle of each turn shaft and balance the multi-joint arm according to the detected turn angles.

In consideration of the problems of the related art, the present invention provides an automatic balancing structure of a medical balancing stand, capable of independently establishing a balance on each horizontal turn shaft without using an encoder or a computer.

According to an aspect of the present invention, the medical balancing stand includes a first arm and a second arm, the second arm having a turn shaft which is horizontally fitted into a predetermined position of the first arm and with which the second arm is turnable relative to the first arm, a first end of the second arm supporting a load, a second end of the second arm having an adjustment unit to balance the second arm on the turn shaft. The automatic balancing structure of the medical balancing stand includes a lever that is attached to the turn shaft, is positionally fixed to the second arm, and has a contact part at a front end thereof, a turn plate that is attached to the turn shaft so as to freely turn around the turn shaft and has a pair of stoppers that are in contact with the contact part and hold the contact part, a clutch unit that is fixed to the first arm and engages with a part of the turn plate to lock the turn plate, and a strain sensor that is arranged on the lever, detects a strain occurring on the lever, and according to the detected strain, outputs a signal to the adjustment unit to balance the second arm. In a normal state, the turn plate turns with the lever. In a balance adjusting state to cancel an imbalance, the clutch unit locks the turn plate and the strain sensor detects a strain occurring on the lever due to torque generated by the imbalance.

DESCRIPTION OF PREFERRED EMBODIMENTS

An automatic balancing structure of a medial balancing stand according to an embodiment of the present invention will be explained with reference to the drawings.

Figure 1:
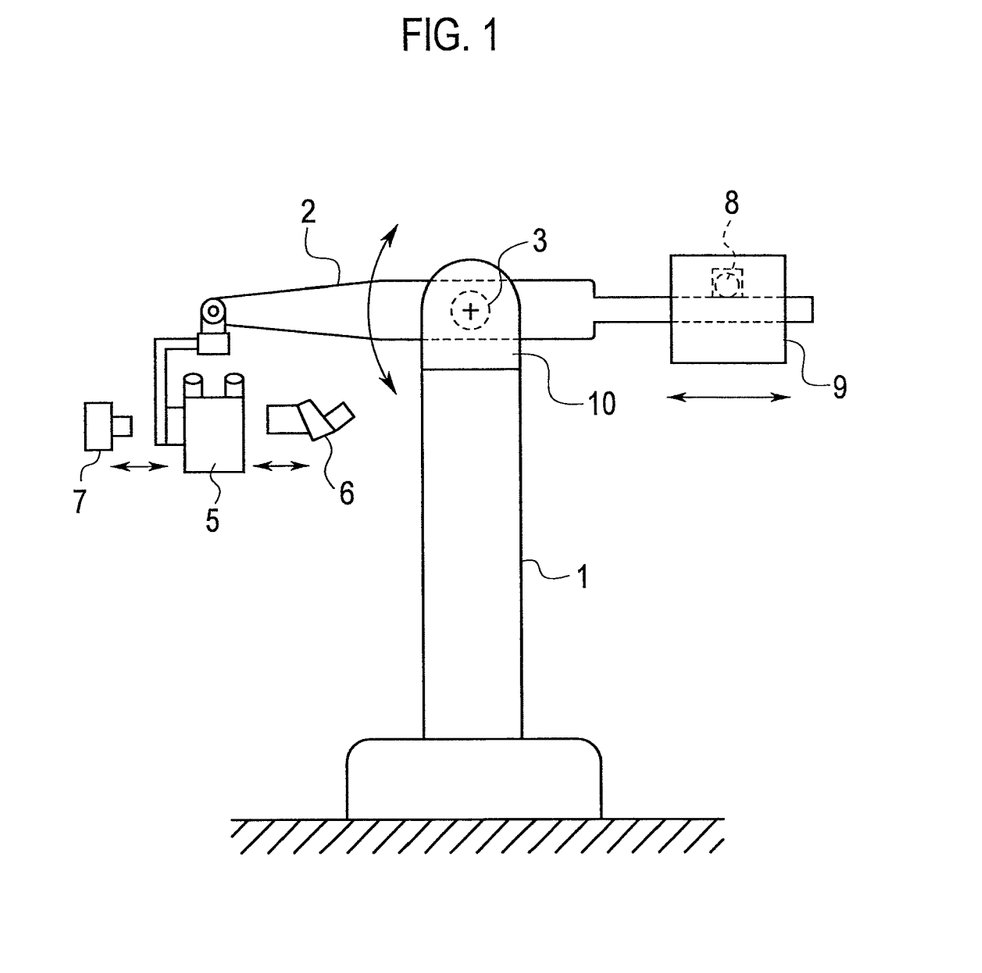
FIG. 1 is a side view illustrating a medical balancing stand employing an automatic balancing structure according to an embodiment of the present invention.

In FIG. 1, the medical balancing stand includes a vertical arm 1 (corresponding to the "first arm" in the claims) that is fixed relative to, for example, a floor that has a predetermined positional relationship with respect to a gravitational direction. An upper end of the vertical arm 1 rotatably supports an intermediate part of a lateral arm 2 (corresponding to the "second arm" in the claims). The lateral arm 2 integrally has a turn shaft 3 that horizontally passes through the upper part of the vertical arm 1, supported with a bearing 4, and defines a virtual rotational axis of the lateral arm 2. Namely, a main axis of the turn shaft 3 is horizontally fixed with respect to the vertical arm 1 and the lateral arm 2 is turnable around the main axis of the turn shaft 3.

A first end of the lateral arm 2 supports a relatively heavy load such as a surgical microscope 5, a side microscope 6, and a camera 7. The side microscope 6 and camera 7 are detachably attached to the surgical microscope 5. When these items are detached from the surgical microscope 5, the weight of the load changes.

A second end of the lateral arm 2 has a counterweight 9 that is moved by a motor 8. The motor 8 and counterweight 9 form the "adjustment unit" stipulated in the claims.

Figure 4:
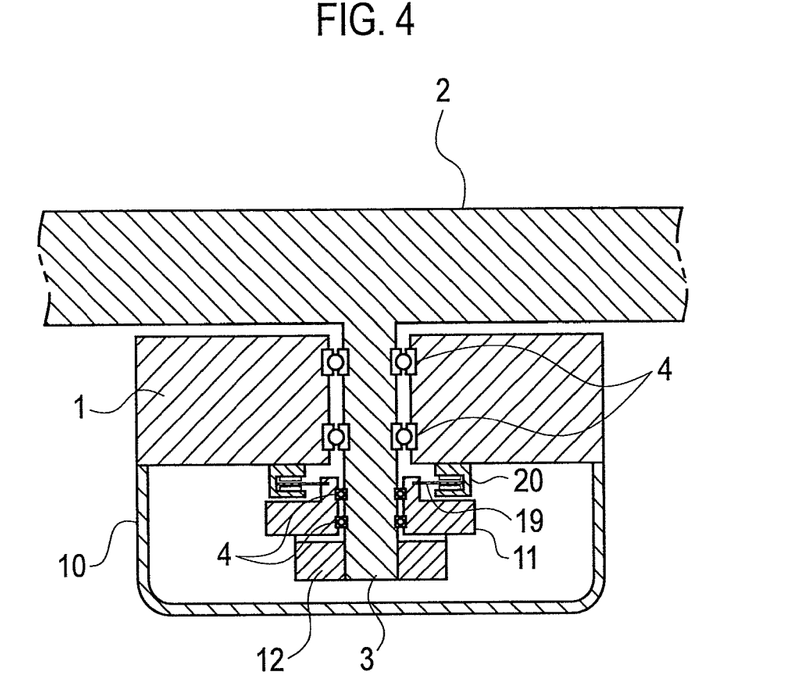
FIG. 4 is a sectional view along a line SA-SA of FIG. 2.
Figure 5:
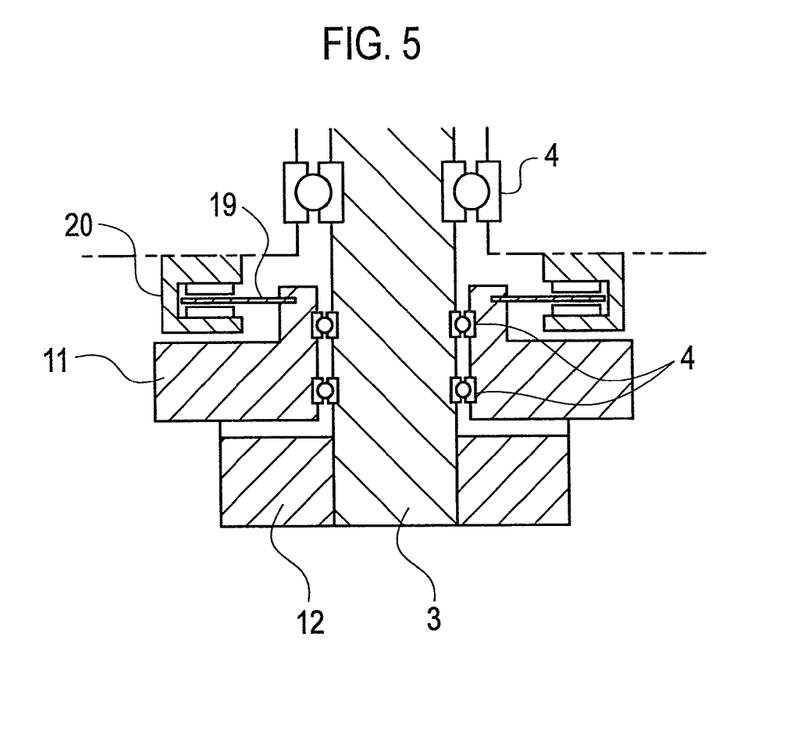
FIG. 5 is an enlarged sectional view illustrating part of the lever and turn plate of FIG. 4.

The upper end of the vertical arm 1 where the turn shaft 3 of the lateral arm 2 horizontally passes through is covered with a cover 10 (FIG. 4). Inside the cover 10, a turn plate 11 is supported with a bearing 4 so that the turn plate 11 is turnable relative to the turn shaft 3.

A front end of the turn shaft 3 is passed through the turn plate 11 and is fixed to a lever 12 that turns together with the turn shaft 3. Namely, the lever 12 is fixed through the turn shaft 3 relative to the lateral arm 2, and therefore, a position (angle) of the lever 12 reflects a position of the lateral arm 2.

Figure 2:
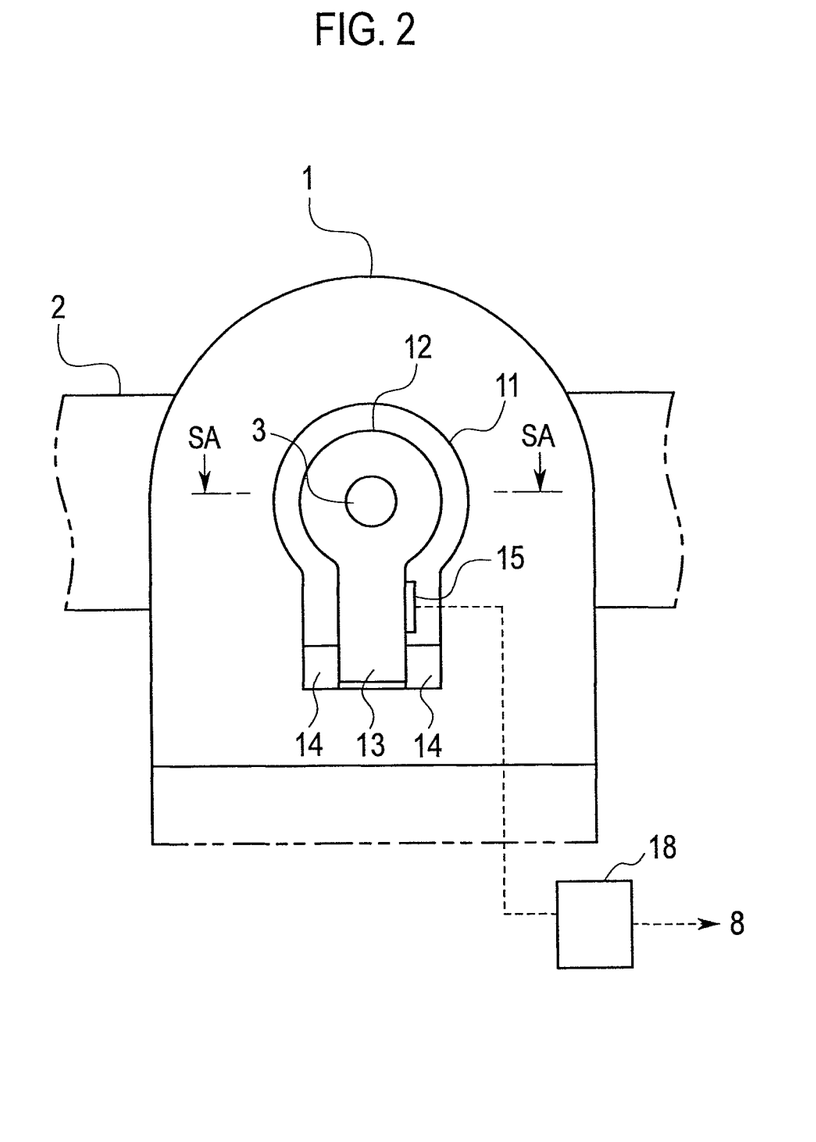
FIGS. 2 and 3 are front and perspective views illustrating a lever and turn plate of the automatic balancing structure.
Figure 3:
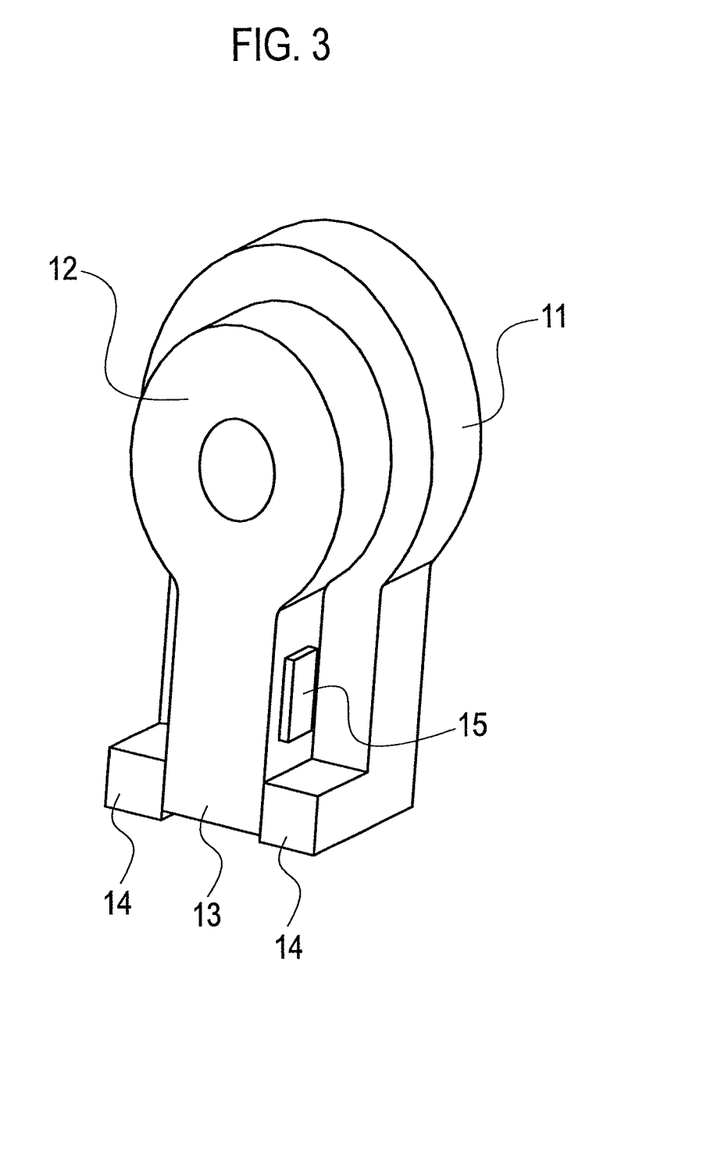

The lever 12 integrally has a contact part 13 that downwardly extends when the lateral arm 2 is horizontal. On each side of the contact part 13, the turn plate 11 has a stopper 14 that is in contact with and holds the contact part 13.

Figure 8:
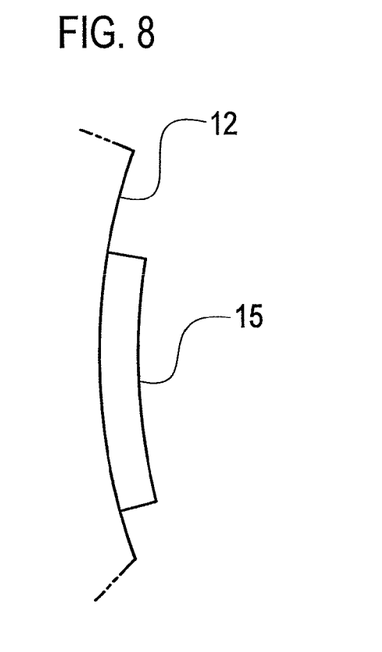
FIG. 8 is an enlarged view illustrating a strain sensor arranged on the lever.

A strain sensor 15 such as a strain gauge is adhered to a side face of the lever 12. The strain sensor 15 is connected through a controller 18 to the motor 8 that moves the counterweight 9. According to a signal from the strain sensor 15, the controller 18 determines the magnitude of a strain occurring on the lever 12 and drives the motor 8 accordingly.

The back of the turn plate 11 is provided with a circular flange 19 around the turn shaft 3. The vertical arm 1 is fixedly provided with a clutch 20. When instructed, the clutch 20 holds and locks the flange 19 so that the turn plate 11 becomes immovable around the turn shaft 3. The flange 19 and clutch 20 form the "clutch unit" stipulated in the claims.

Operation of the automatic balancing structure according to the embodiment will be explained.

When the clutch 20 is released, the turn plate 11 is turnable. In this state, the contact part 13 and stoppers 14 are in contact with each other, and therefore, the turn plate 11 and lever 12 turn together to follow a movement of the turn shaft 3 of the lateral arm 2. When the turn plate 11 is freely turnable, the lever 12 causes no strain.

Figure 6:
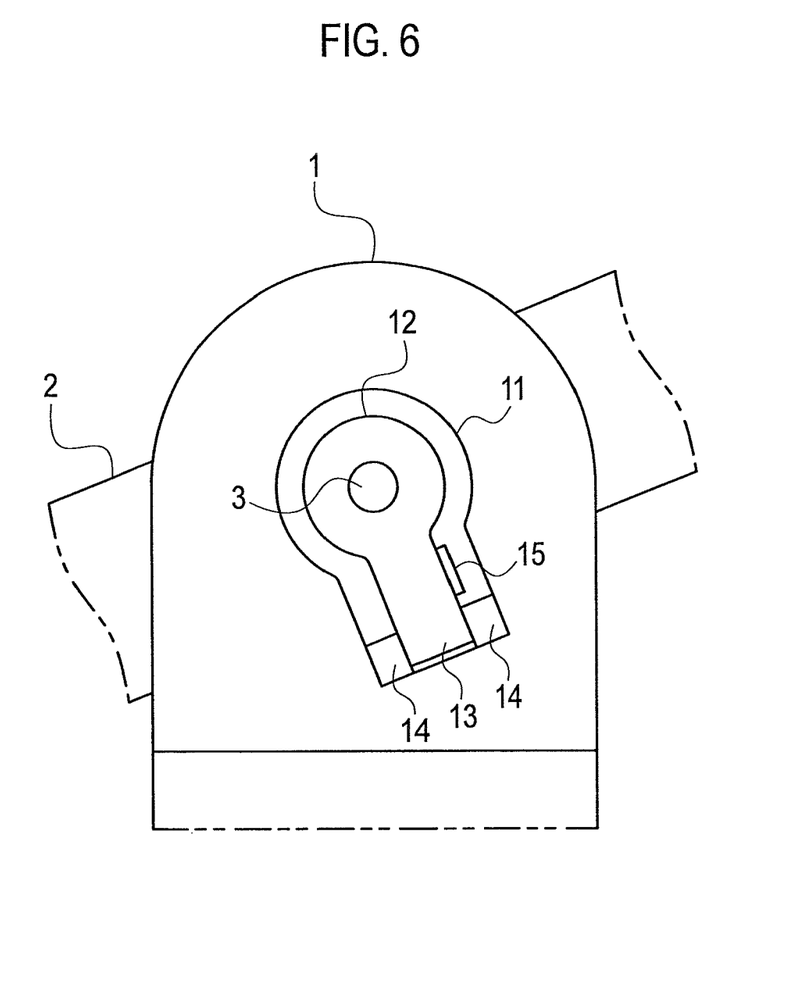
FIG. 6 is a front view illustrating the lever, turn plate, and lateral anti turned together from the state of FIG. 2.

When a doctor or an operator who manipulates the surgical microscope 5 wants to change a vertical position of the surgical microscope 5, the doctor turns the lateral arm 2. To achieve this, the doctor pushes a button (not illustrated) on the surgical microscope 5 to release the clutch 20 and turns the lateral arm 2 by holding and moving the surgical microscope 5. Since the surgical microscope 5 is balanced with the counterweight 9, the doctor can easily and lightly turn the lateral arm 2.

At a required position, the doctor removes his or her hands from the surgical microscope 5, which stops at the position because the lateral arm 2 having the surgical microscope 5 is balanced. When the doctor releases his or her finger from the button (not illustrated) on the surgical microscope 5, the clutch 20 locks the flange 19 of the turn plate 11 to fix the lateral arm 2 at the position.

When the clutch 20 is locked, the lateral arm 2 is almost unable to turn because the contact part 13 of the lever 12 is in face-to-face contact with the stoppers 14 of the turn plate 11.

If the side microscope 6 or the camera 7 is attached to or detached from the surgical microscope 5, the balanced state breaks into an imbalanced state that must be corrected.

To attach or detach, for example, the camera 7, the clutch 20 is first locked. When the camera 7 is attached to or detached from the surgical microscope 5, the balance of the lateral arm 2 on the turn shaft 3 breaks to cause torque about the rotational axis 3 to turn the lateral arm 2.

Figure 7:
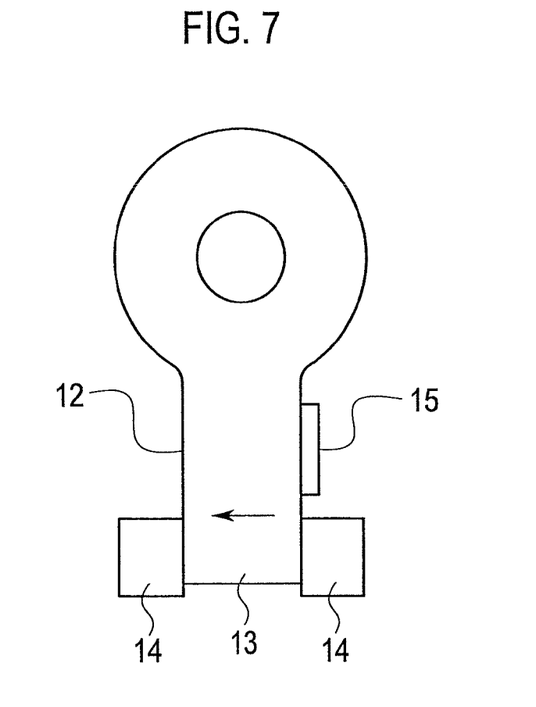
FIG. 7 is a view illustrating the lever under strain.

The torque of the lateral arm 2 in the imbalanced state acts through the stopper 14 of the turn plate 11 onto the contact part 13 to generate torque on the lever 12 around the rotational axis 3. This torque generates stress on the lever 12 and contact part 13 extending from the turn shaft 3 to the stopper 14. This stress causes a strain on the lever 12 in a compression or tension direction. The strain is detected by the strain sensor 15, which outputs a signal indicating the magnitude and direction of the strain. According to the direction of the strain, it is possible to detect a direction of the torque. According to this embodiment, the strain sensor 15, i.e., a dynamic sensor arranged on the lever 12 detects a strain caused by torque, converts the detected strain into an electrical signal, and sends the signal through a preamplifier to the controller 18.

Namely, when the strain sensor 15 detects a strain $\epsilon$, the strain sensor 15 outputs a signal representing the strain to the controller 18. According to the signal, the controller 18 controls and drives the motor 8 to move the counterweight 9 in a direction to remove the strain and correct an imbalance. When the imbalance is corrected to a balanced state, no strain exists on the lever 12. Accordingly, the counterweight 9 is stopped at the position and the lateral arm 2 is balanced on the turn shaft 3.

After the camera 7 or the like is attached to or detached from the surgical microscope 5 and the balanced state is reestablished, the clutch 20 may be released to vertically adjust the surgical microscope 5.

In this way, the embodiment employs no encoder or computer. Only with the strain sensor 15, the embodiment adjusts the balance of the lateral arm 2 on the turn shaft 3. Accordingly, the embodiment is capable of downsizing the medical balancing stand. The balancing operation according to the embodiment is easy to carry out at high speed and is stable and reliable.

If the lateral arm 2 is a multi-joint arm having a plurality of horizontal turn shafts, the embodiment is capable of independently achieving the balancing operation on each of the turn shafts and thereby totally balancing the multi-joint arm.

In this way, the present invention employs no encoder or computer. Instead, the present invention employs a strain sensor to easily establish a balanced state and downsize the automatic balancing structure of the medical balancing stand. Even if the medical balancing stand employs a multi-joint lateral arm having a plurality of horizontal turn shafts, the present invention is able to separately adjust the turn shafts to balance the multi-joint lateral arm on the turn shafts.

According to the present invention, the stoppers hold the contact part of the lever, and therefore, the lever and turn plate turn together to follow a movement of the second arm (lateral arm) without bothering the movement of the second arm. In a balanced state, the second arm having the turn shaft turns with light force relative to the first arm (vertical arm), and when an operator removes his or her hands from the second arm, stops at the position. The stopped state of the second arm may be locked with the clutch unit. In the locked state, the second arm causes no play, and in this state, the medical balancing stand can safely be moved for storage or transportation.

If the second arm is put into an imbalanced state, the clutch unit is used to lock the turn plate. As a result, the turn plate becomes immovable and the lever tries to turn due to torque generated by the imbalanced state, thereby creating a strain on the lever. The strain is detected by the strain sensor, which outputs a signal to the adjustment unit. According to the signal, the adjustment unit acts to solve the imbalanced state and restore the balanced state.

The adjustment unit according to the present invention employs the movable counterweight that simplifies the adjustment unit.

This patent application claims the benefit of priority under 35 U.S.C. 119(a) to Japanese Patent Application No. 2012-268091 filed on Dec. 7, 2012 whose disclosed contents are incorporated by reference herein.

What is claimed is:

1. An automatic balancing structure of a medical balancing stand, the medical balancing stand having a first arm and a second arm, the second anti turnable about a turn shaft that is horizontally fixed relative to the first arm, a first end of the second arm supporting a load, a second end of the second arm having an adjustment unit to balance the second arm about the turn shaft, the automatic balancing structure comprising:

a lever fixed through the turn shaft relative to the second arm and having a contact part at a front end thereof;

a turn plate rotatably fixed to the turn shaft and having a pair of stoppers that are in contact with the contact part and hold the contact part;

a clutch unit fixed relative to the first arm and engaging with a part of the turn plate to lock the turn plate; and a strain sensor arranged on the lever, detecting a strain occurring on the lever, and outputting a signal to the adjustment unit to balance the second arm about the turn shaft according to the detected strain, wherein in a normal state, the turn plate turns with the lever, in a balance adjusting state to cancel an imbalance, the clutch unit locks the turn plate and the strain sensor detects a strain occurring on the lever due to torque caused by the imbalance.

2. The automatic balancing structure of the medical balancing stand of claim 1, wherein the adjustment unit includes a counterweight that is arranged at the second end of the second arm and is movable according to the signal from the strain sensor so as to balance the second arm.

* * * * *

UNITED STATES PATENT AND TRADEMARK OFFICE
CERTIFICATE OF CORRECTION

PATENT NO.        : 8,979,042 B2                                      Page 1 of 1
APPLICATION NO.   : 14/095467
DATED             : March 17, 2015
INVENTOR(S)       : Doi et al.

It is certified that error appears in the above-identified patent and that said Letters Patent is hereby corrected as shown below:

In the claims

Column 4, line 61 claim 1, line 3 change "anti turnable" to -- arm turnable --.

Signed and Sealed this
Fifteenth Day of December, 2015

Michelle K. Lee
*Director of the United States Patent and Trademark Office*